United States Patent [19]

Kubota et al.

[11] Patent Number: 4,979,952
[45] Date of Patent: Dec. 25, 1990

[54] ULTRASONIC VIBRATION TREATMENT APPARATUS

[75] Inventors: Tatsuya Kubota; Syuichi Takayama; Shinji Hatta, all of Tokyo; Masakazu Gotanda, Sagamihara; Hitoshi Karasawa; Hiroshi Sasaki, both of Tokyo; Tadao Hagino, Yokohama; Hiroki Hibino, Tokyo, all of Japan

[73] Assignee: Olympus Optical Co., Ltd., Tokyo, Japan

[21] Appl. No.: 494,880

[22] Filed: Mar. 8, 1990

Related U.S. Application Data

[63] Continuation of Ser. No. 158,914, Feb. 22, 1988, abandoned.

[30] Foreign Application Priority Data

| Mar. 2, 1987 | [JP] | Japan | 62-46980 |
| Mar. 2, 1987 | [JP] | Japan | 62-46981 |
| Mar. 2, 1987 | [JP] | Japan | 62-46986 |
| Nov. 27, 1987 | [JP] | Japan | 62-299239 |

[51] Int. Cl.$^5$ ............................................. A61B 17/32
[52] U.S. Cl. ................................. 606/169; 310/316; 318/116; 128/24 AA
[58] Field of Search ............ 606/169, 170, 128; 128/4–9, 24 A; 73/632, 655; 331/65; 310/316, 317, 323; 318/116; 604/20, 22

[56] References Cited

U.S. PATENT DOCUMENTS

| 2,728,220 | 12/1955 | Willner | 73/655 |
| 4,577,508 | 3/1986 | Chaplin | 73/655 |
| 4,579,000 | 4/1986 | Sudo |  |

FOREIGN PATENT DOCUMENTS

| EP0139753A1 | 5/1985 | European Pat. Off. . |
| 1623410 | 3/1971 | Fed. Rep. of Germany . |
| 2916540 | 10/1979 | Fed. Rep. of Germany . |
| 3100669 | 1/1982 | Fed. Rep. of Germany . |
| 61-51668 | 3/1961 | Japan . |
| 54-140526 | 10/1979 | Japan . |

Primary Examiner—C. Fred Rosenbaum
Assistant Examiner—William W. Lewis
Attorney, Agent, or Firm—Frishauf, Holtz, Goodman & Woodward

[57] ABSTRACT

An ultrasonic vibration treatment apparatus comprising an ultrasonic vibration treatment device including an ultrasonic vibrator and an ultrasonic wave transmitter probe, a detecting element opposing the transmitter for applying light to the transmitter and receiving the light reflected from the transmitter, thereby to detect the amplitude of vibration of the treatment device, and a power source controller for reducing the power supplied to the vibrator, or stopping the power supply to the vibrator, in accordance with a detection signal output by the detecting element. The detecting element quickly detects the charges in the amplitude of vibration of the ultrasonic vibration treatment device, said charge in the amplitude representing the charges in the vibration condition of the vibration treatment device from actual driving to idling, or vice versa. The power source controller fast responds to the detection signal output by the element, and immediately controls the treatment device in idling state, so as to prolong the lifetime of the treatment device.

8 Claims, 16 Drawing Sheets

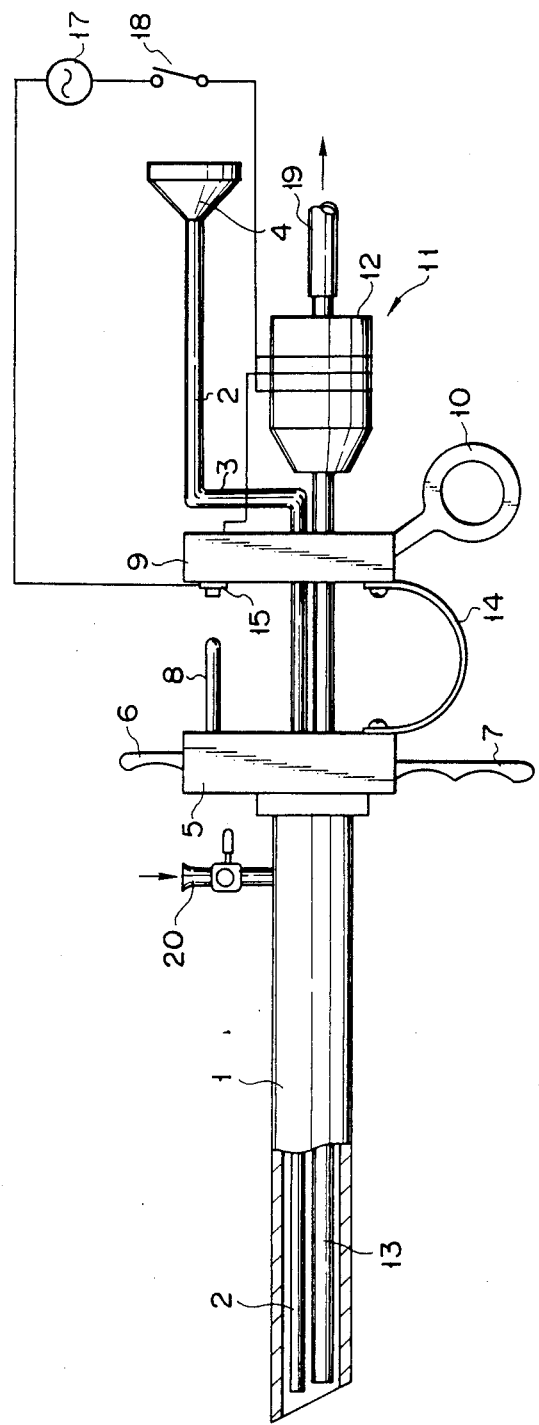
F I G. 1

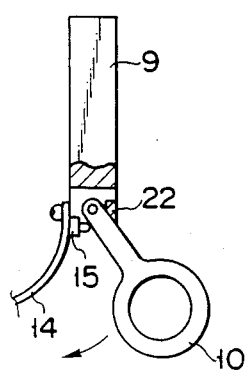 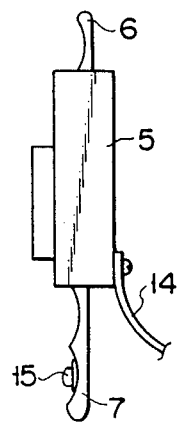 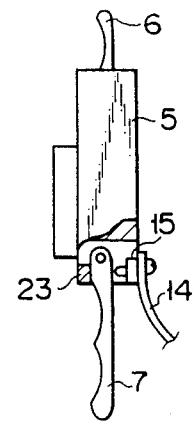
FIG. 3   FIG. 4   FIG. 5
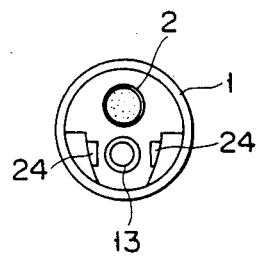 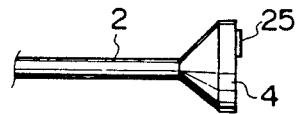
FIG. 6   FIG. 7

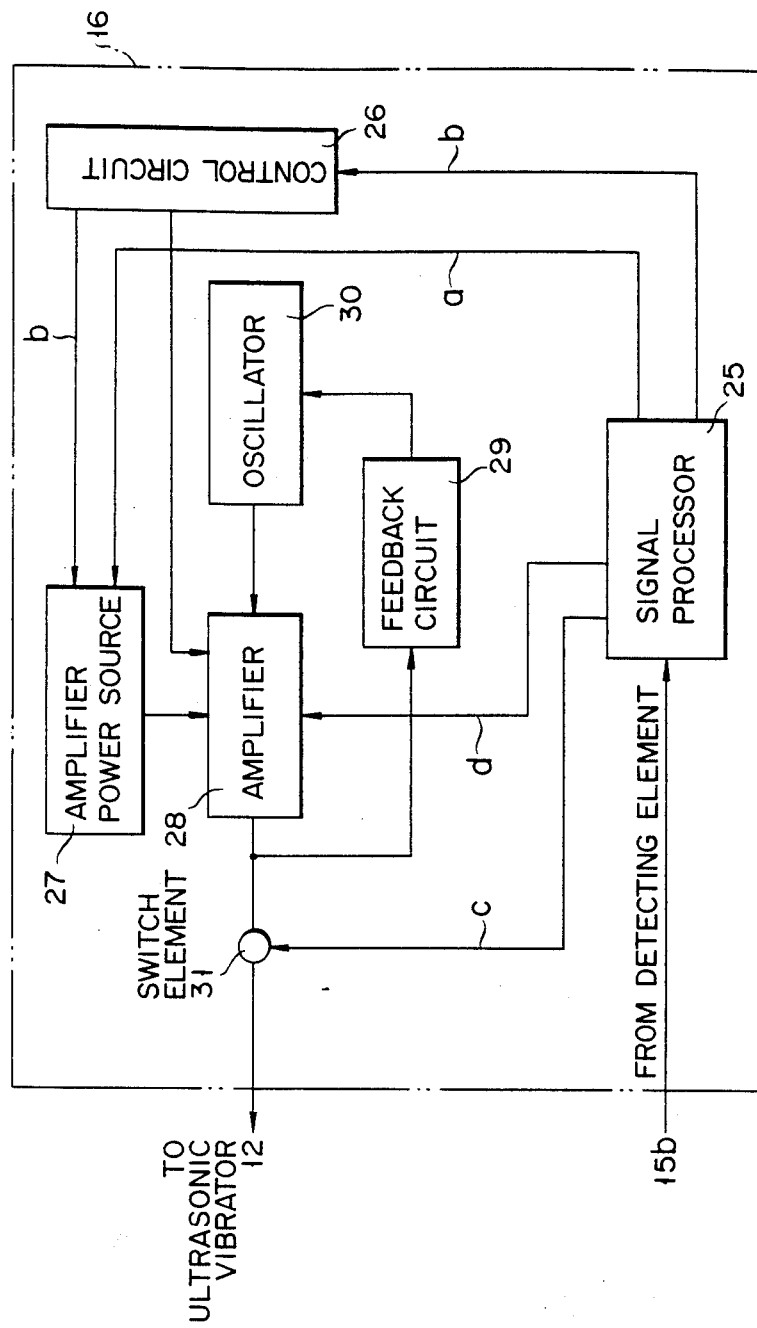
F I G. 12

ULTRASONIC VIBRATION TREATMENT APPARATUS

This application is a continuation of application Ser. No. 07/158,914, filed Feb. 22, 1988, now abandoned.

BACKGROUND OF THE INVENTION

1. Field of the Invention

This invention relates to an ultrasonic vibration treatment apparatus for effecting a treatment of a living structure, for instance such medical treatment as removal of a hypertrophic prostate or destruction of a calculus, by utilizing ultrasonic vibrations.

2. Description of the related art

Ultrasonic vibration treatment apparatuses, in which a treatment device for removing or destructing a diseased portion of the man's body, e.g., a hypertrophic prostate or a calculus, by utilizing ultrasonic vibrations is assembled in an endoscope, are well known in the art and in practical use. Such a treatment apparatus comprises a ultrasonic vibrator and a probe, e.g., a metal pipe, as a treatment device coupled to the vibrator for transmitting ultrasonic vibrations therefrom. In operation, the distal end of the probe undergoing ultrasonic vibrations with the operation of the vibrator, is directly urged against the diseased portion of the body for the removal or destruction of that portion.

In the prior art ultrasonic vibration treatment apparatus of the above construction, however, the amplitude of vibrations produced in the probe is greatly different at the time of actual driving, in which the distal end of the probe is held urged against the diseased portion for removal or destruction thereof, and at the time of idling, in which the probe is vibrated with its distal end not urged against but spaced apart from the diseased portion. This is so because the resistance offered to the probe is different between the above two instances. At the time of idling, substantially no resistance is offered to the probe. Therefore, the probe is vibrated with a very large amplitude compared to the amplitude at the time of actual driving. In consequence, the repetitive stress produced in the probe is increased, thus leading to early wear of the probe due to metallic fatigue.

A piezoelectric vibrator drive circuit disclosed, for instance, in Japanese Patent Disclosure Sho 54-140,526 (West German Patent Specification No. 2,916,540), is provided with an aim of overcoming the drawback noted above. The disclosed circuit makes use of a contact relation which is found between the drive current caused through the vibrator and the vibration amplitude. The vibration amplitude of the treatment device is controlled by controlling the drive current through the vibrator to be constant. In this way, early wear of the device such as heat generation or destruction can be prevented. Means for electromagnetically detecting the amplitude of ultrasonic vibrations are disclosed in U.S. Pat. Specification No. 4,579,000 and U.S. Pat. Application Ser. No. 20,333 filed Feb. 27, 1987 by the present applicant. In the former means, a coil is formed such that it surrounds a projection of ion or like magnetic material provided on a vibrator. In this case, vibrations of the projection accompanying the vibrations of the vibrator are measured as a change in the coil current. In the latter means, a permanent magnet is provided on a vibratory portion, i.e., part of vibrator or treatment device, and a coil is formed such that it surrounds the permanent magnet. In this case, vibrations of the permanent magnet are detected as a change in the coil current for measuring the amplitude of vibrations.

By using the above means, it is possible to control the vibration amplitude by controlling the drive current according to the measurement of vibrations of the vibratory portion. In this method of electromagnetic measurement of the vibration amplitude, however, extra components such as a magnet which are undesired in view of the status of vibration are directly mounted on the vibrator or treatment device. Consequently, the weight and shape of the vibrator or treatment device are changed to change the resonant frequency or impedance characteristics. Further, the characteristics values of the vibrator usually are not fixed due to fluctuations in manufacture. This means that the same vibration amplitude can not be obtained by setting the same current, and the desired vibration amplitude can not be obtained unless a current value is set for each vibrator. In some cases, the setting of a current leads to unexpected destruction of the vibrator. At any rate, it is difficult to permit stable control of the vibration treatment device.

SUMMARY OF THE INVENTION

An object of the invention is to provide a supersonic vibration treatment apparatus, which can detect the vibrating state and immediately control the vibration of an ultrasonic vibration treatment device as a medium of ultrasonic vibrations to prevent said treatment means from being vibrated with a large amplitude at the time of transmission from the actual drive state over to the idling state of the treatment device.

Another object of the invention is to provide an ultrasonic vibration treatment apparatus, which can detect or measure vibrations of a vibratory part affecting the status of vibration and stably control the vibration of a vibrator according to the detected or measured value.

To attain the first object noted above, there is provided an ultrasonic vibration treatment apparatus, which comprises detecting means for detecting a change in the operating or vibrating state of an ultrasonic vibratory part (i.e., a vibrator or a vibration treatment device) and control means capable of controlling the vibration of an ultrasonic vibrator immediately according to a signal from the detecting means.

To attain the second object noted above, there is provided an ultrasonic vibration treatment apparatus, which comprises means for projecting light onto the ultrasonic vibrator, means for detecting or measuring the vibration of the vibration treatment device according to reflected light from said vibrator and control means for controlling the driving of said supersonic vibrator according to a detected or measured value.

BRIEF DESCRIPTION OF THE DRAWINGS

FIG. 1 is a side view, partly in section, showing a first embodiment of the ultrasonic vibration treatment apparatus according to the invention;

FIGS. 3 to 7 are fragmentary views showing respective third to seventh embodiments of the ultrasonic vibration treatment apparatus according to the invention;

FIG. 12 is a block diagram showing a power source controller assembled in the apparatus of FIG. 11;

DETAILED DESCRIPTION OF THE PREFERRED EMBODIMENTS

Figure 2:
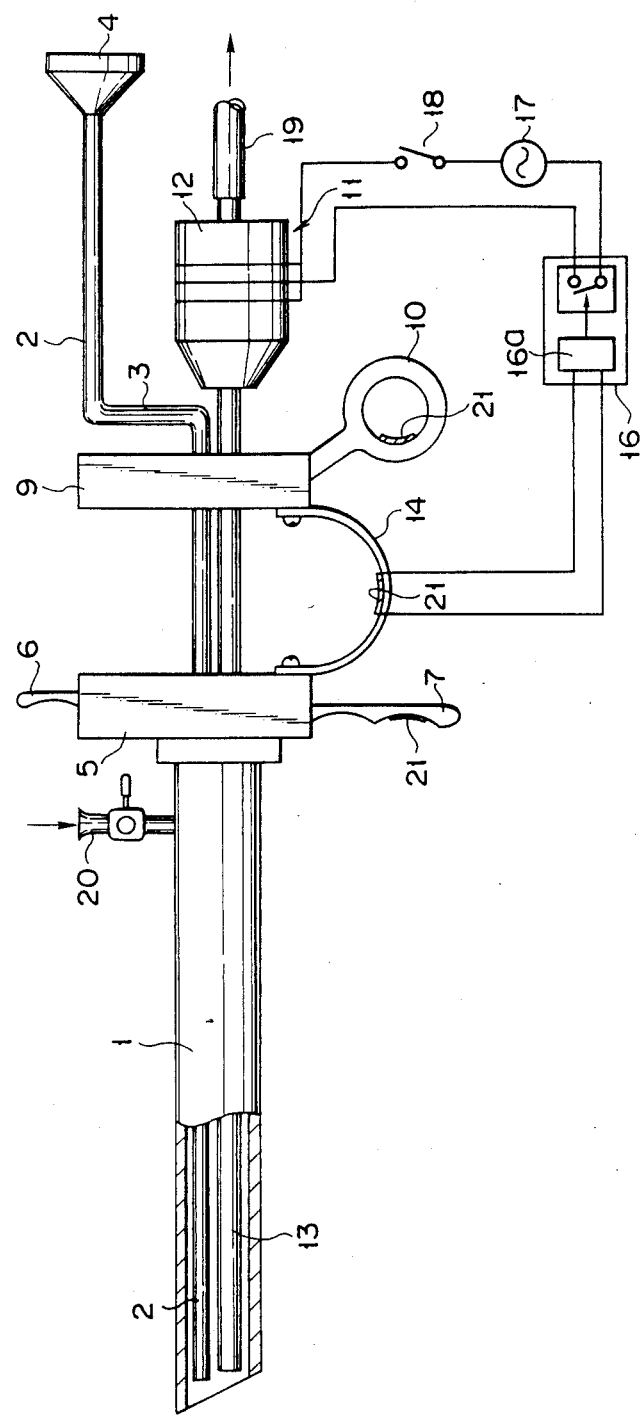
FIG. 2 is a view similar to FIG. 1 but showing a second embodiment of the ultrasonic vibration treatment apparatus according to the invention.

FIG. 1 shows a first embodiment of the ultrasonic vibration treatment apparatus according to the invention. The illustrated apparatus comprises sheath 1. Optical viewing tube 2 is inserted in sheath 1. Optical viewing tube 2 includes intermediate upright portion 3 and provided at a stem with objective section 4. As a whole, it constitutes an endoscope in a crank-like form. An intermediate portion of optical viewing tube 2 is supported in a support 5 provided on a stem of sheath 1.

Support 5 is provided with upper and lower finger application pieces 6 and 7. It is also provided with operating rod 8 projecting from its back side. Slider 9 is slidably mounted on a portion of optical viewing tube 2 extending rearwardly from support 5. Slider 9 is provided with downwardly projecting rear finger application piece 10, and is also integrally provided with supersonic vibration treatment device 11. Ultrasonic vibration treatment device 11 consists of ultrasonic vibrator 12 and probe 13 consisting of a metal pipe. Probe 13 is coupled to and vibrated by ultrasonic vibrator 12 and serves as a ultrasonic vibration trans-mitter. It slidably penetrates a mounting hole (not shown) formed in support 5. Thus, ultrasonic vibration treatment device 11 and slider 9 are slidable forwardly in unison with each other.

Between support 5 and slider 9, there is provided substantially U-shaped curved leaf spring 14. Slider 9 can be moved against the restoring force of leaf spring 14. The surface of slider 9 facing support 5 is provided at a position corresponding to operating rod 8 with first switch 15, which serves as detecting means. First switch 15 is adapted to be struck and turned on by operating rod 8 when slider 9 is moved forwardly to a predetermined extent. At this time, first switch 15 provides a signal to turn on power source 17, whereupon power is supplied to ultrasonic vibrator 12. The power source circuit of power source 17 includes second switch 18.

Suction tube 19 is connected to the rear surface of ultrasonic vibrator 12 and communicated with probe 13. The other end of suction tube 19 is connected to a suction pump (not shown). Sheath 1 is provided at the stem with water supply plug 20. Through water supply plug 20 cooling water is supplied to probe 13. The supplied cooling water is withdrawn through suction tube 19.

When using the ultrasonic vibration treatment apparatus having the above construction, second switch 18 is turned on, and the endoscope is held with a hand by applying the index finger to upper finger application piece 6, the middle, medical and little fingers to lower finger application piece 7 and the thumb to rear finger application piece 10. Then, sheath 1 is inserted into the body for observing the inside of the body through objective section 4 of optical viewing tube 2. If a portion requiring a treatment, e.g., a hypertrophic prostate or a calculus, is found, the hand holding the endoscope is gripped. As a result, ultrasonic vibration treatment device 11 is moved in unison with slider 9 against the restoring force of leaf spring 14, and the distal end of probe 13 projects from the distal end of sheath 1.

When the distal end of probe 13 is projected to a predetermined extent from sheath 1, it touches the portion to be treated such as a prostate or a calculus, while first switch 15 provided on slider 9 is turned on by operating rod 8. As a result, current is supplied from power source 17 to ultrasonic vibrator 12. Ultrasonic vibrator 12 thus generates an ultrasonic wave to cause ultrasonic vibration of probe 13, so that removal of the prostate or destruction of the calculus can be effected.

It is to be appreciated that since the ultrasonic vibration treatment apparatus of the above construction uses ultrasonic vibration treatment device 11, first switch 15 is turned on to cause ultrasonic vibration of probe 13 when and only when probe 13 is projected from sheath 1 by gripping the hand holding the endoscope. In other words, probe 13 can be vibrated when and only when ultrasonic vibration treatment device 11 is in an operative state for removing a prostate or destructing a calculus, it is possible to prevent idling vibrations of probe 13.

FIG. 2 shows a second embodiment of the invention. In this instance, strain gauges 21 are provided in lieu of first switch 15 as detecting means on lower and rear finger application pieces 7 and 10 and leaf spring 14. When a strain is produced in strain gauges 21 as a result of operation of treatment device 11, resistance detector 16a in controller 16 detects the strain to produce a detection signal to render a relay circuit operative, whereby power is supplied to ultrasonic vibrator 12. In other words, ultrasonic vibrator 12 is energized when fingers are applied to finger application pieces 7 and 10 and ultrasonic vibration treatment device 11 is moved forwardly.

FIG. 3 shows a third embodiment of the invention. In this instance, rear finger application piece 10 is provided rotatably on slider 9, and its rotation is restricted by stopper 22. Further, first switch 15 is provided on slider 9. When the hand holding the endoscope is gripped to cause rotation of rear finger application piece 10, first switch 15 provided on slider 9 is turned on to energize ultrasonic vibrator 12.

FIG. 4 shows a fourth embodiment of the invention. In this instance, first switch 15 is provided on lower finger application piece 7.

FIG. 5 shows a fifth embodiment of the invention. In this instance, lower finger application piece 7 is provided rotatably on support 5 such that its rotation is restricted by stopper 23. When it is rotated, first switch 15 provided on support 5 is turned on.

FIG. 6 shows a sixth embodiment of the invention. In this instance, photo-sensor 24 is provided at the distal end of sheath 1, in which probe 13 is inserted. When probe 13 projects from the distal end of sheath 1, it is detected, whereupon power is supplied to ultrasonic vibrator 12.

FIG. 7 shows a seventh embodiment of the invention. In this instance, photo-sensor 25 is provided on objective section 4 of optical viewing tube 2. When an operator looks through objective section 4, photo-sensor 25 detects this to produce a detection signal so as to energize ultrasonic vibrator 12.

Although not shown, it is possible two or more of the detecting means shown in FIGS. 1 to 7 such that probe 13 is vibrated when and only when all the provided detecting means are turned on. In this case, it is possible to reliably prevent idling vibrations.

Further, when detecting means is turned on, this may be displayed by turning on a light-emitting diode or the like. Doing so can improve the operability and safety. The light-emitting diode in this case may be provided on optical viewing tube 2 or ultrasonic vibration treatment device 11.

Second switch 18 in the first embodiment may be omitted. As has been shown, with this embodiment of the invention, when an operation necessary for the use of the ultrasonic vibration treatment apparatus is done, it is detected, and the operation of the ultrasonic vibrator is controlled according to the detection signal. In other words, when and only when an operation for the use of the ultrasonic vibration treatment apparatus is done, the ultrasonic vibrator can be rendered operative, so that it is possible to eliminate early damage to the ultrasonic vibrator due to idling or a hazard of unexpected driving of the apparatus.

Figure 8:
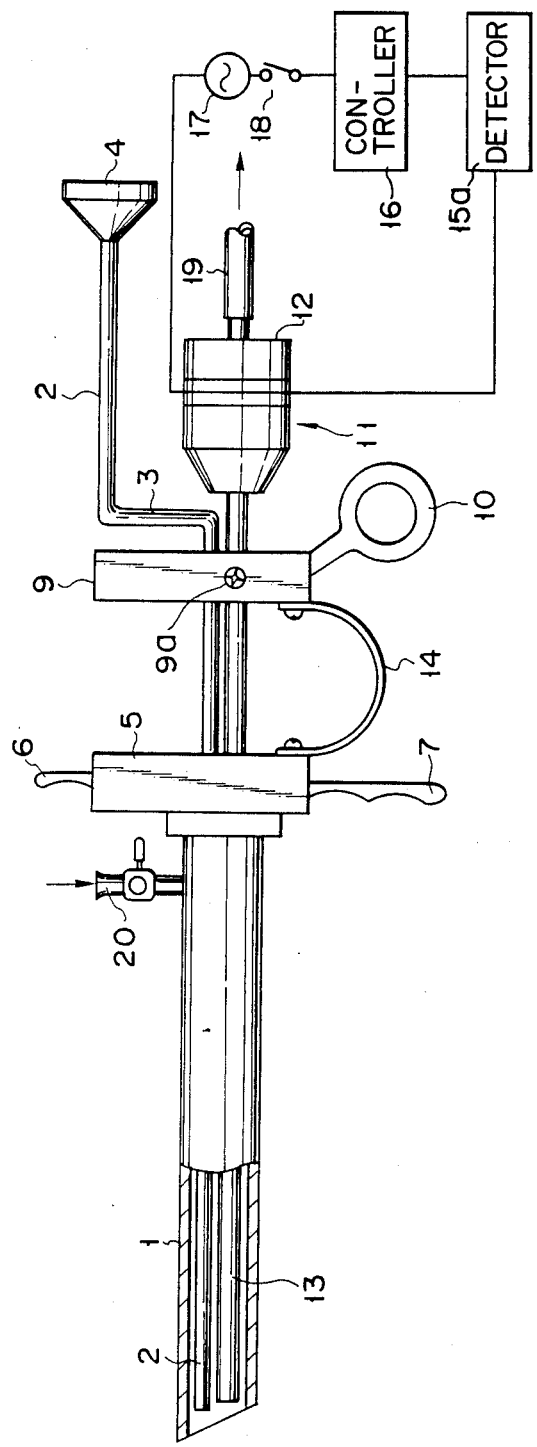
FIG. 8 is a view similar to FIG. 1 but showing a still further embodiment of the ultrasonic vibration treatment apparatus according to the invention.

FIG. 8 shows a further embodiment of the ultrasonic vibration treatment apparatus according to the invention. This embodiment is the same as the preceding embodiments so long as a vibration treatment device consisting of a vibrator and a probe is assembled in an endoscope. Therefore, like parts are designated by like reference numerals, and their description is omitted.

In this embodiment, detector 15a is connected to ultrasonic vibrator 12 as means for detecting the impedance of an oscillating circuit assembled in ultrasonic vibrator 12 at the time of resonance of the oscillating circuit. A detection signal from detector 15a is supplied to controller 16. Power source 17 for supplying power to ultrasonic vibrator 12 is controlled by controller 16 in the manner as described later. Main switch 18 is provided between controller 16 and power source 17.

Figure 9:
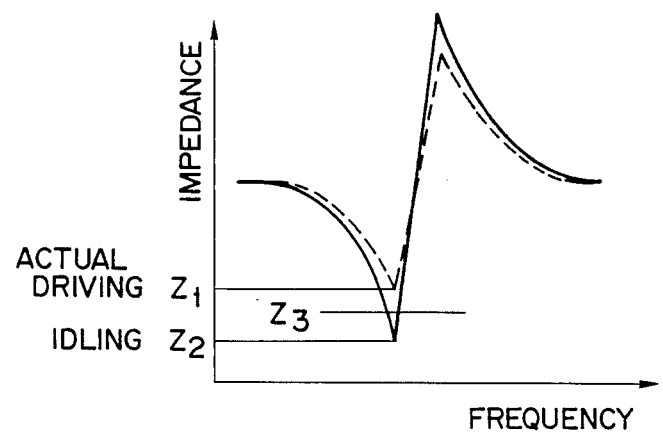
FIG. 9 is a graph for explaining the variation of impedance of a vibrator drive circuit in the apparatus of FIG. 8 at the time of resonance between actual drive state and idling state.

The impedance of ultrasonic vibrator 12 at the time of resonance of the oscillating circuit as detected by detector 15a, is different at the time of actual drive, at which a load is applied to probe 13, and at the idling time, at which no load is applied. More specifically, the vibration frequency and impedance has the relationship shown in FIG. 9, and the impedance at the time of resonance has value $Z_1$ higher value $Z_2$ at the time of actual drive as shown by dashed line, than at the time of idling as shown by solid line. Controller 16 controls power source 17 such that power for driving ultrasonic vibrator 12 is increased when the impedance detected by detector 15a satisfies a relation $Z_2 < Z_3 < Z_1$ and exceeds $Z_3$ while it is reduced when the impedance becomes lower than $Z_3$. The value $Z_3$ of impedance is determined empirically.

Thus, when probe 13 of ultrasonic vibration treatment device 11 is caused to undergo ultrasonic vibration in contact with a portion to be treated, that is, actually driven, the impedance at resonance, which is detected at this time by detector 15a, has a value $Z_1$ higher than $Z_3$. As a result, high drive power is supplied from power source 17 to ultrasonic vibrator 12. Probe 13 is thus vibrated with a sufficient strength to treat the portion to be treated.

At the idling time, at which probe 13 is not in contact with any portion to be treated, the impedance at resonance as detected by detector 15a is lower than $Z_3$. As a result, power supplied to ultrasonic vibrator 12 is reduced to reduce the amplitude of vibrations of probe 13. It is thus possible to prevent great repetitive stress from being produced in probe 13.

Figure 10:
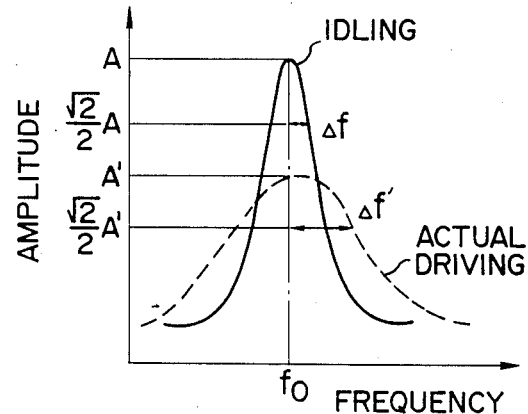
FIG. 10 is a graph showing the variation of the Q value (keenness) at the time of resonance between the states noted above.

FIG. 10 shows the relationship between the frequency (f) and amplitude (A) of the vibration of the ultrasonic vibrator undergoing a resonance operation. From this relationship, the amplitude keenness at the time of resonance operation, i.e., Q value (f0/Δf), can be obtained. The Q value is greater when no load is exerted on the vibrator as is indicated by the solid line, than when load is applied to the vibrator as is shown by the dashed line. Hence, if the power supplied to ultrasonic vibrator 12 is increased when the Q value becomes less than the value shown by the solid line, probe 13 can be operated as efficiently as in the above embodiments. If the power is decreased when the Q value becomes greater than the value shown by the dashed line, probe 13 can be protected from damage, as reliably as in the above embodiments.

In each of the embodiments described above, the power input to ultrasonic vibrator 12 is reduced when it is detected, from the impedance or the Q value, that probe 13 is idling. According to the invention, the supply of power to vibrator 12 can be stopped as soon as probe 13 is found to be idling.

As has been shown, with this embodiment of the invention the impedance or Q value of the ultrasonic vibration treatment device consisting of the ultrasonic vibrator and ultrasonic vibration transmitter at the time of the resonance of the device is detected, and power supplied to the ultrasonic vibrator is controlled when it is detected from the detected impedance or Q value that the ultrasonic vibration transmitter is idling. It is thus possible to prevent the ultrasonic vibrator (i.e., probe) from being vibrated with a large amplitude at the time of idling, thus eliminating the possibility of early fatigue and rupture of the ultrasonic vibration transmitter.

Figure 11:
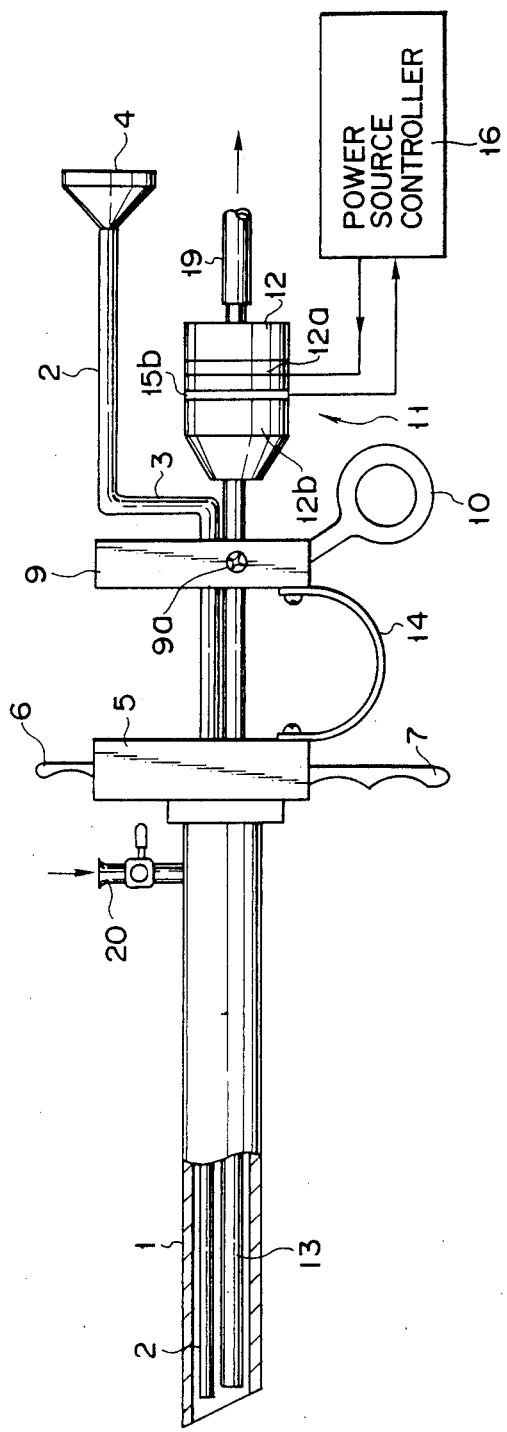
FIG. 11 is a view similar to FIG. 1 but showing a yet further embodiment of the ultrasonic vibration treatment apparatus according to the invention.

FIG. 11 shows a further embodiment of the ultrasonic vibration treatment apparatus. In this instance, ultrasonic vibrator 12 is provided with detecting element 15b as detecting means for detecting the amplitude of its vibration. Detecting element 15b consists of piezoelectric rubber, for instance. It may be applied to the outer periphery of ultrasonic vibrator 12, or it may be clamped between vibrating element 12a and horn 12b constituting ultrasonic vibrator 12.

A detection signal from detecting element 15b is supplied to power source controller 16. Power source controller 16 has a structure as shown in FIG. 12. As is shown, it has signal processor 25, to which the signal from detecting element 15b is supplied. Control circuit 26, amplifier power source 27 and amplifier 28 are connected to signal processor 25. Amplifier 28 receives a signal from oscillator 30 and provides a drive signal to ultrasonic vibrator 12. The drive signal provided from amplifier 28 is fed back through feedback circuit 29 to oscillator 30.

When the amplitude of vibration of ultrasonic vibrator 12 as detected by detecting element 15b is above a predetermined value, that is, when it is detected that probe 13 is idling, signal processor 25 provides a control signal for controlling the amplitude of vibration of ultrasonic vibrator 12. The contents of the control signal are roughly classified into first control, through which the oscillation of ultrasonic vibrator 11 is stopped, and second control, through which the amplitude of vibration of ultrasonic vibrator 12 is controlled to a constant small amplitude. The first control may be effected by turning off amplifier power source 27 as shown by line a, turning off amplifier power source 27 through control circuit 26 as shown by line b or turning on switch element 31, which may be a relay provided in a line for supplying a drive signal from amplifier 28 to ultrasonic vibrator 12, as shown by line c. The second control may be effected by reducing the drive signal from amplifier 28 through control thereof as shown by line d or controlling amplifier power source 27 through control circuit 26 such as to reduce output of amplifier power source 27.

The ultrasonic vibration treatment apparatus having the above construction can be used in the same manner as the previous embodiments. More specifically, by holding the endoscope part of the apparatus, sheath 1 is inserted into the body, and the body inside is observed through objective section 4 of optical viewing tube 2. When a portion to be treated is found, a main switch (not shown) of power source controller 16 is turned on. The portion to be treated, e.g., a prostate or a calculus, is removed or destroyed by applying the distal end of probe 13, which is projected from the distal end of Sheath 1 and under ultrasonic vibration, to the portion to be treated.

If probe 13 is idling, i.e., vibrated with its distal end not contacting the portion to be treated, probe 13 is vibrated with a greater amplitude compared to the case of the actual drive. Detecting element 15b immediately detects such a vibration amplitude change to provide a detection signal supplied to signal processor 25 of the power source controller 16. The signal processor 25 processes the input detection signal to produce a control signal for controlling the amplitude of vibration of ultrasonic vibrator 12. The contents of the control signal may be the first control for stopping the vibration of ultrasonic vibrator 12 as shown by [lines a to c in FIG. 2] or the second control for reducing the vibration amplitude of ultrasonic vibrator 12 to a predetermined amplitude. In consequence, the vibration of probe 13 is stopped or weakened, so that it is possible to prevent probe 13 from being continuously vibrated with a large amplitude and damaged.

Figure 13:
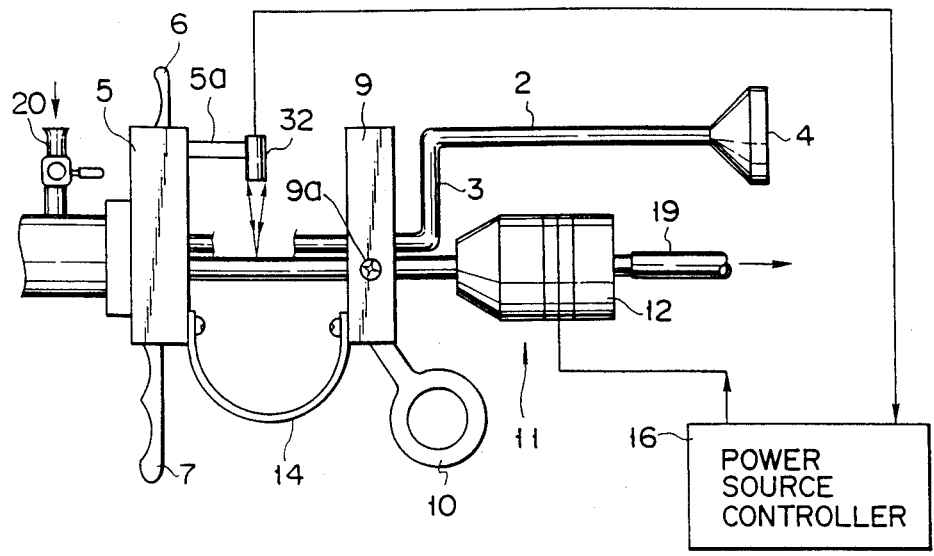
FIG. 13 is a fragmentary side view showing a further embodiment of the ultrasonic vibration treatment apparatus, in which an optical sensor is used as vibration detection means.

FIG. 13 shows a further embodiment of the invention. In this instance, support 5 supports detecting element 32 consisting of an optical sensor via support arm 5a. Detecting element 32 detects the amplitude or frequency of vibration of probe 13.

Figure 14:
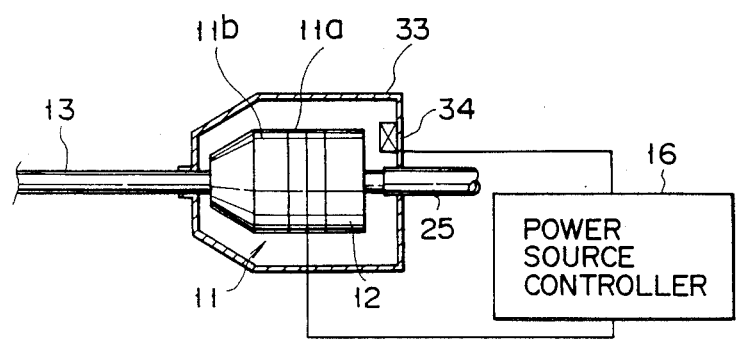
FIG. 14 is a fragmentary sectional view, to an enlarged scale, showing a different example of the vibration detection means.

FIG. 14 shows a still further embodiment of the invention. In this instance, ultrasonic vibrator 12 is covered by cover 33 provided with microphone 34. Microphone 34 picks up the vibration sound of ultrasonic vibrator 12, and its output is passed through a filter circuit (not shown) to detect only sound in the neighborhood of the resonant frequency. The amplitude of vibration is detected according to the volume of the detected sound.

Further, although not shown, a strain gauge may be applied to probe 13 for detecting a strain due to vibrations of probe 13.

As has been shown, with this embodiment of the invention the amplitude of vibration of the ultrasonic vibration treatment device consisting of the ultrasonic vibrator and ultrasonic vibration transmitter is detected, and the vibration of the ultrasonic vibrator is controlled when it is detected from the detected signal that a predetermined value is exceeded by the amplitude of vibration. It is thus possible to prevent the ultrasonic vibrator from being idled to be continuously vibrated with a large amplitude, thus eliminating the possibility of early damage to the ultrasonic vibration transmitter.

Figure 15:
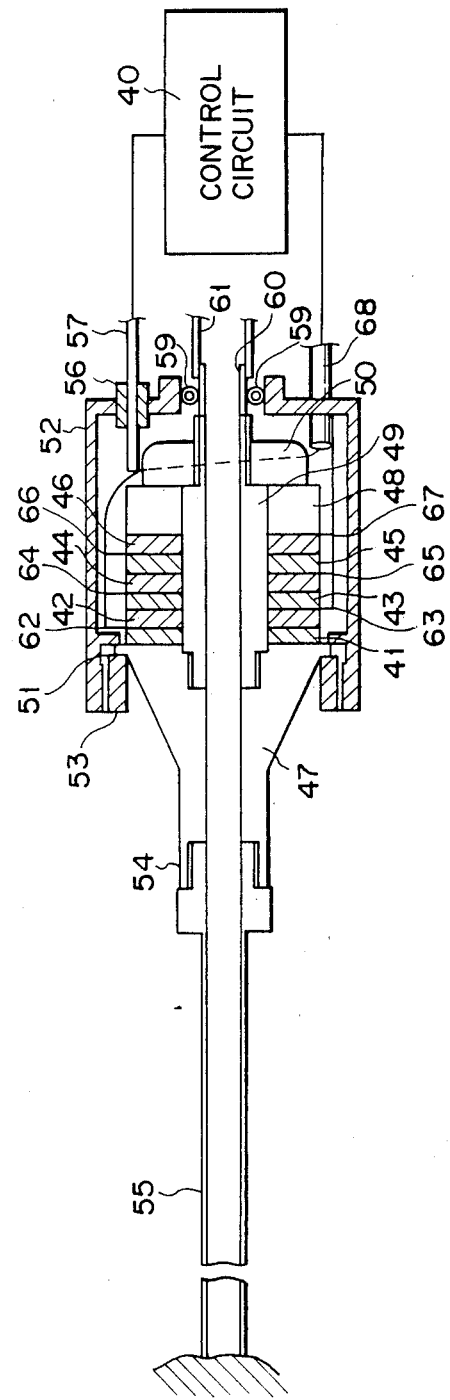
FIG. 15 is a sectional view, partly in section, showing a still another embodiment of the ultrasonic vibration treatment apparatus according to the invention.

FIG. 15 shows a further embodiment of the ultrasonic vibration treatment apparatus according to the invention. The Figure shows only the vibration treatment device of the apparatus, i.e., the ultrasonic vibrator and probe coupled thereto, that is, it shows only the vibratory part of the apparatus.

In this instance, the ultrasonic vibrator is a Langevin type vibrator consisting of first to sixth piezoelectric elements 41 to 46. First to sixth piezoelectric elements 41 to 46 are clamped between horn 47 and back support member 48 and tightened together by bolt 49 and nut 50. The tightening force reaches as high as several 100 kg. Horn 47 serves to amplify the vibrations, and back support member 48 serves to adjust the resonant frequency of the vibrator.

Horn 47 has flange 51, which is secured by nut 53 to vibrator case 52. Probe 55, to which ultrasonic vibrations are transmitted, is coupled by screw 54 to the end of horn 47.

The rear end of case 52 is provided with bushing 56. Fiber 57 (made of glass or plastics) securedly penetrates bushing 56 such that its end is spaced apart a predetermined distance from and faces back support member 48. The rear end of fiber 57 is connected to a drive circuit to be described later, and light from a light source is led through fiber 57 to be incident on the rear surface of back support member 48. The vibration of the vibrator can be measured by detecting the intensity of the reflected light.

Figure 17:
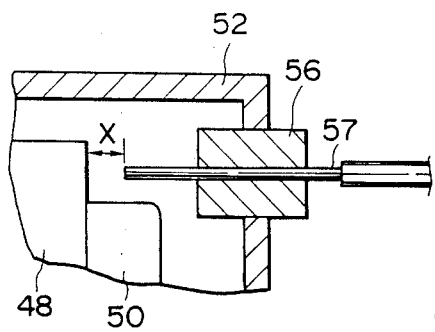
FIG. 17 is a view illustrating an example of the method of securement of a fiber used in light projection means of the ultrasonic vibration treatment apparatus of FIG. 15.

The method of securing fiber 57 will now be described. FIG. 17 shows one example of the method. Fiber 57 securely penetrates bushing 56 such that its end is held at a predetermined distance x from back support member 48.

Figure 18:
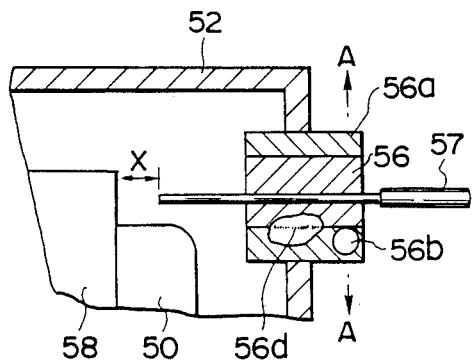
FIG. 18 is a view illustrating a different example of the method of securement.
Figure 19:
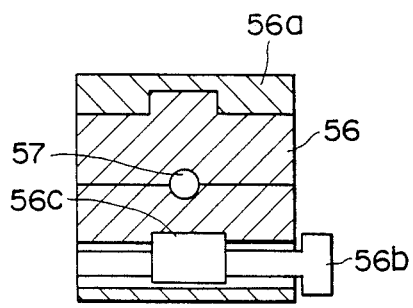
FIG. 19 is a sectional view, to an enlarged scale, taken along line A—A in FIG. 18.

FIG. 18 and FIG. 19 (which is a sectional view taken along line A—A in FIG. 18) show another example of the method. In this case, slide base 56a is provided on bushing 56 such that the distance x between fiber 57 and back support member 48 is adjustable through pinion-and-rack mechanism 56c provided on screw 56b by turning screw 56b. The distance x can be measured by scale 56d, which is provided on bushing 56 and slide base 56a.

For accurate measurement of vibration, even a slight error of the distance x between fiber 57 and back support member 48 is not allowed. With this instant arrangement, an error $\Delta x$ of the distance x can be corrected to permit measurement of the amplitude with the accurate distance x provided between fiber 57 and back support member 48.

The ultrasonic vibrations generated in the vibrator are liable to be transmitted to fiber 57 through case 52 to interfere with the measurement of vibration. For this reason, bushing 56 is suitably made of an elastic material capable of absorbing vibrations. Bushing 56 and slide base 56a may be displaced relative to each other by other means than the rack-and-pinion mechanism.

Referring back to FIG. 15, probe 55 is hollow and communicates with through holes formed in horn 47 and bolt 49. The rear end of bolt 49 is connected to pipe-like member 60, which is in turn connected to case 52 via O-ring 59 and also connected to suction tube 61. Suction tube 61 is connected to a suction pump (not shown), and removed tissues and the like are withdrawn from the probe space through the suction tube.

Piezoelectric elements 41 to 46 are provided with electrodes 62 to 67, which are connected through coaxial cable 68 to a drive power source control circuit 40 to be described later. In this embodiment, electrodes 62, 64 and 66 are connected to the inner conductor of coaxial cable, and electrodes 63, 65 and 67 to the outer conductor of the coaxial cable.

Figure 16:
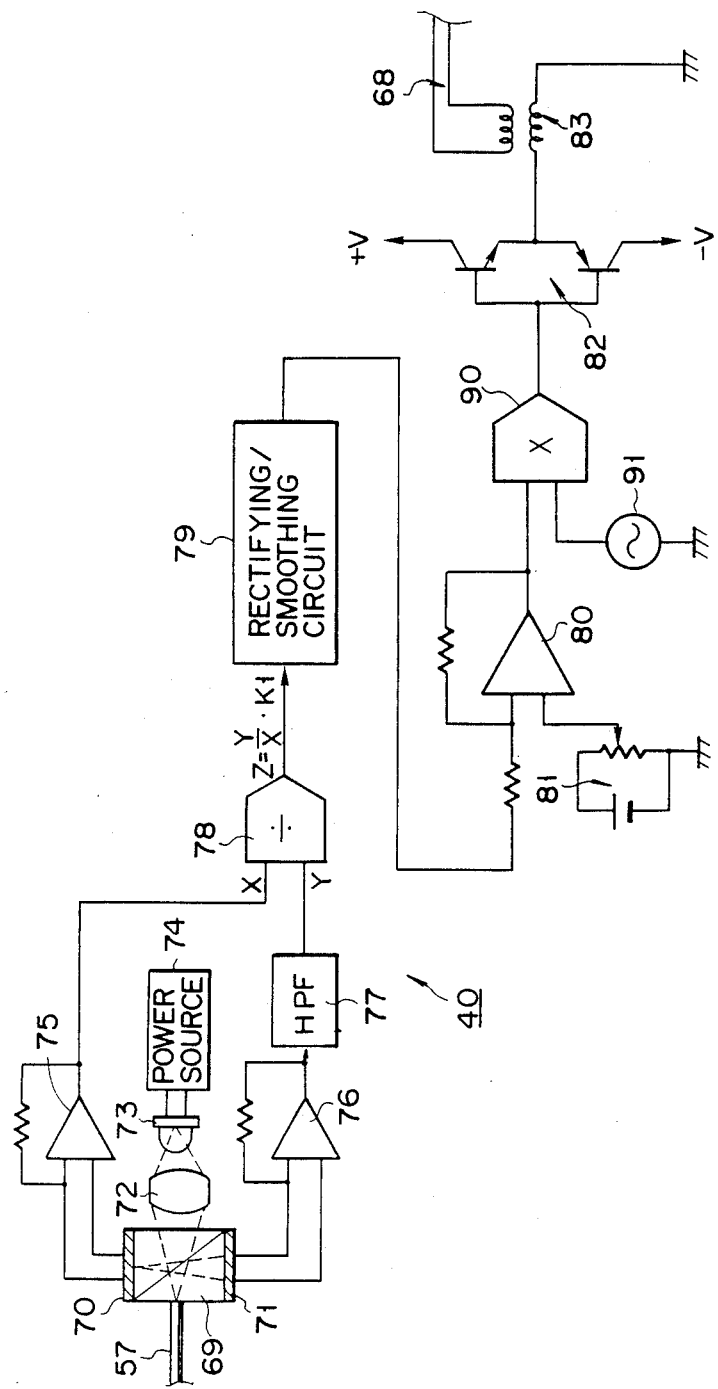
FIG. 16 is a schematic representation of a power source controller in the ultrasonic vibration treatment apparatus of FIG. 15.

FIG. 16 shows the control circuit 40 noted above. The rear end of fiber 57 is connected to one end of half prism 69, which has its opposite side surfaces provided with respective first and second light-receiving elements 70 and 71. Behind the other end of half prism 69, there are provided lens 72 and light-emitting diode (LED) 73. Power source 74 is connected to LED 73. Light emitted from LED 73 is split by half prism 69 into a transmitted light beam and a reflected light beam. The transmitted light is incident on the rear end of fiber 57, while the reflected light is incident on light-receiving element 70. Light incident from fiber 57 on half prism 69 is reflected by half prism 69 to be incident on light-receiving element 71.

Outputs of light-receiving elements 70 and 71 are coupled to amplifiers (current/voltage converters) 75 and 76. The output of amplifier 75 is supplied to divider 78 directly, while the output of amplifier 76 is supplied through high-pass filter (HRF) 77 to divider 78. The output of divider 78 is supplied to rectifying/smoothing circuit 79, the output of which is in turn supplied to a first input terminal of differential amplifier 80. Reference power supply 81 is connected to a second input terminal of differential amplifier 80. Reference power supply 81 is a variable power supply, and it provides a reference voltage which corresponds to a reference value of drive current supplied to the vibrator as will described later in detail.

The output of differential amplifier 80 is supplied to a first input terminal of multiplier 90. The output of oscillator 91, which oscillates at a constant frequency, is supplied to a second input terminal of multiplier 90. The output of multiplier 90 is supplied to power amplifier 82. The output of power amplifier 82 is coupled through transformer 83 to the rear end of coaxial cable 68. In other words, the output of power amplifier 82 is coupled through transformer 83 and coaxial cable 68 to electrodes 62 to 67 of piezoelectric elements 41 to 46 to provide the drive current through the vibrator.

Now, the operation of this embodiment will be described with reference to FIGS. 20 and 21. In this treatment apparatus, basically the amplitude of vibration of the vibrator consisting of piezoelectric electric elements 41 to 46 is amplified by horn 47 under the principles of the Langevin type vibrator, and the distal end of treatment device 55 is vibrated with a large amplitude for the destruction of the object of treatment. For this reason, the vibrations of the vibrator should be controlled adequately in dependence on the status of the object of treatment.

Figure 20:
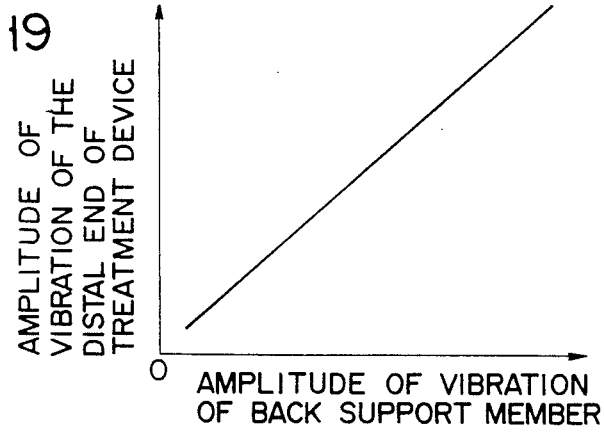
FIG. 20 is a graph showing a relation between the amplitude of vibration of the distal end of a vibration treatment device and amplitude of vibration of a back support member in the ultrasonic vibration treatment apparatus of FIG. 15.

The amplitude of vibration of the distal end of treatment device 55 and amplitude of vibration of back support member 48 are in a fixed relation to each other, as shown in FIG. 20, provided that the load on the distal end is fixed and the supplied power is a third parameter. Therefore, the amplitude of vibration of treatment device 55 can be measured by measuring the amplitude of vibration of back support member 48. In this embodiment, the vibration of back support member 48 is measured by measuring light having been emitted from fiber 57 secured to case 52 and reflected by the vibrating surface.

Light emitted from LED 77 driven by power source 74 is converged by lens 72 to be incident on half prism 69. The reflected light is incident on light-receiving element 70. The transmitted light is incident on fiber 57 to be reflected by the rear end of back support member 48 and be incident on light-receiving element 71. Thus, light-receiving element 70 receives part of light incident on back support member 48, while light-receiving element 71 receives part of the light reflected by back support member 48. The outputs of light-receiving elements 70 and 71 are amplified by amplifiers 75 and 76. The output of amplifier 76 is passed through HPF 77 for removal of the DC component. The output of HPF 77 is supplied together with the output of amplifier 75 to divider 78.

Figure 21A:
FIGS. 21(a) ~ (h) are a waveform charts for explaining the operation of the ultrasonic vibration treatment apparatus of FIG. 15.
Figure 21B:
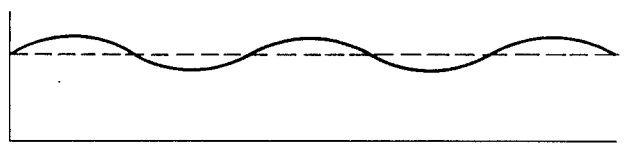
Figure 21C:
Figure 21D:
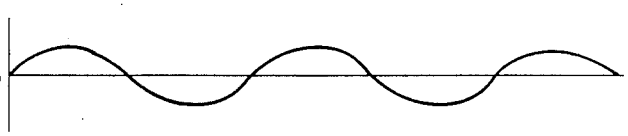

Assuming that the vibration of back support member 48 has a waveform as shown in FIG. 21(a), light-receiving element 71 produces an output signal as shown in FIG. 21(b) according to the vibration. Light-receiving element 70 detects the intensity level of the incident light. Amplifier 75 which amplifies the output of light-receiving element 70 produces an output as shown in (c) in FIG. 21(c). HPF 77, to which the output of light-receiving element 71 is coupled through amplifier 76, produces an output as shown in FIG. 21(d).

Figure 21E:
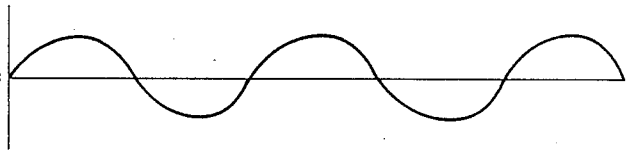

Divider 78 produces an output Z, which is given as $Z = K1 (Y/X)$, where X represents the output of amplifier 75, Y represents the output of HPF 77, and K1 is a constant. Through this division, the intensity level variation of the reflected light due to a change in the light dose of the LED is compensated for. The output of divider 78 is as shown in FIG. 21(e).

Figure 21F:

The output Z of divider 78 is rectified and smoothed in rectifying/smoothing circuit 79 to obtain a DC signal, which is proportional to the amplitude of back support member 48. The DC signal output of rectifying/smoothing circuit 79 is as shown in FIG. 21(f). It is supplied to differential amplifier 80. To differential amplifier 80 is also supplied the reference voltage of reference power supply 81, and differential amplifier 80 compares the DC signal and reference voltage to produce a voltage proportional to the difference.

Figure 21G:
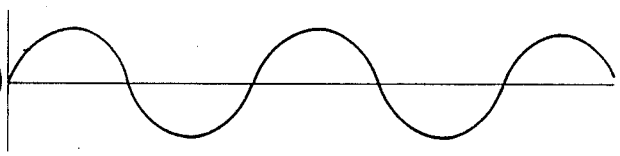
Figure 21H:
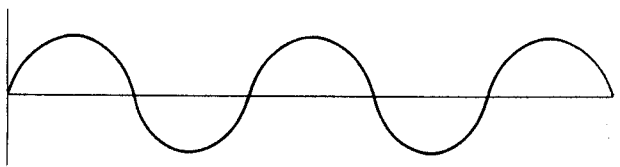

The output of differential amplifier 80 is supplied to multiplier 90 to be multiplied by the output (shown in FIG. 21(g)) of oscillator 91. The output amplitude of oscillator 91 thus is amplified according to the output of differential amplifier 80. The output of multiplier 90 is as shown in FIG. 21(h). The output of multiplier 90 is coupled as is drive signal through power amplifier 82, transformer 83 and coaxial cable 68 to vibrator electrodes 62 to 67.

Thus, when the amplitude of vibration of back support member 48 is increased, the output of rectifying/smoothing circuit 79 exceeds reference voltage 81, so that the output of differential amplifier 80 is reduced to reduce the amplitude of the drive signal. In the converse case, the amplitude of the drive signal is increased. In the above way, multiplier 90 controls the amplitude of the drive signal such as to let the output of rectifying/smoothing circuit 79 coincide with the reference voltage.

As has been shown, in this embodiment the vibration of the vibrator, i.e., the distal end of treatment device 55, is optically measured by contact-free measurement with the arrangement that a laser beam is projected onto the rear end of the vibrator and the reflected beam is received. Desired ultrasonic vibrations thus can be obtained stably through control of the drive signal according to the measured vibration. Further, since the vibration is measured by contact-free measurement, there is no need of providing any extra component on the vibrator or treatment device, and the vibrations can be measured without affecting the status of vibration at all.

Figure 22:
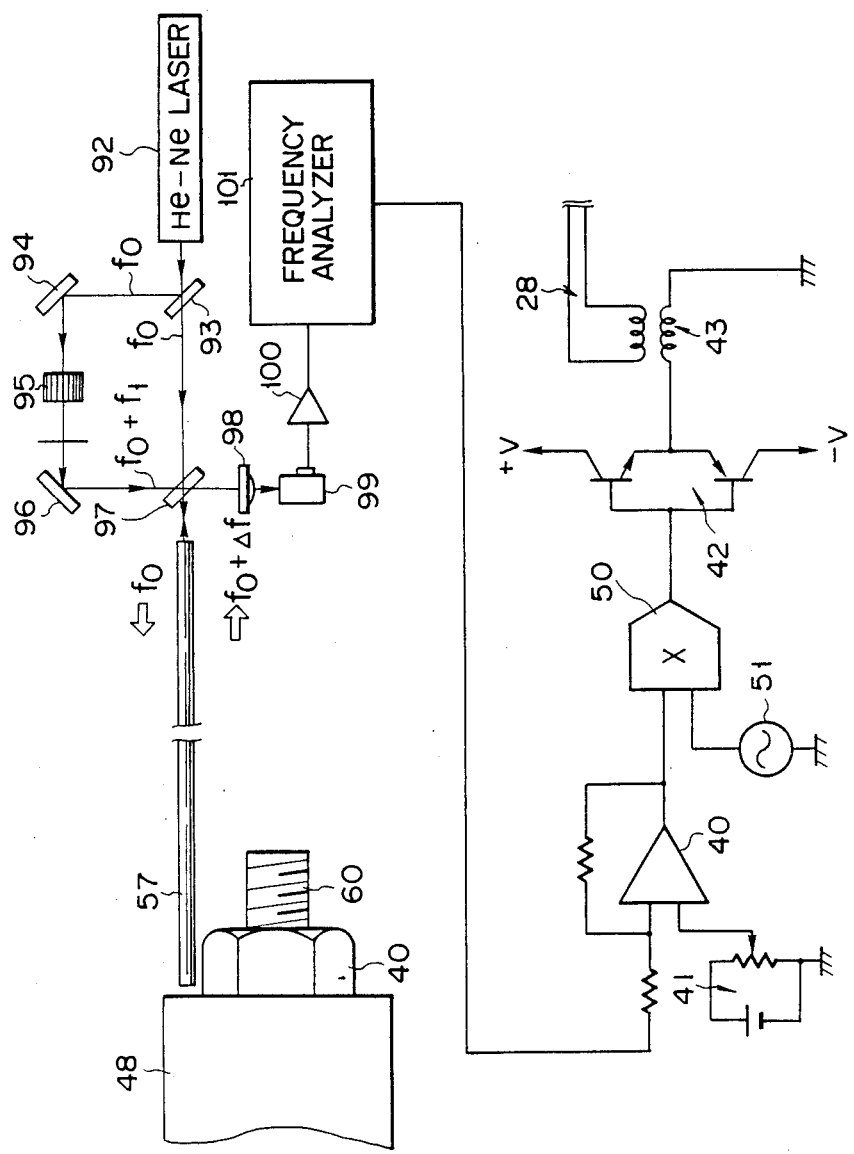
FIGS. 22 and 23 are schematic representations of further embodiments of the ultrasonic vibration treatment apparatus according to the invention.

FIG. 22 shows a further embodiment of the invention. In the Figure, parts like those in the embodiment of FIG. 15 are designated by like reference numerals, and their detailed description is omitted.

In this embodiment, a laser beam from He-Ne laser 92 is transmitted through half mirrors 93 and 97 to be incident on fiber 57. Of the laser beam from He-Ne laser 92, a laser beam reflected by half mirror 93 is led by mirror 94, ultrasonic shifter 95 and mirror 96 to be incident on and transmitted through half mirror 97 before being incident on lens 98. A laser beam having been reflected by back support member 48 and returned through fiber 57, is also reflected by half mirror 97 to be incident on lens 98.

The laser beam incident on lens 98 is photoelectrically converted by photodiode 99 to produce an electric output signal, which is coupled through amplifier 100 to frequency analyzer 101. The output of frequency analyzer 101 is supplied to differential amplifier 80 as noted before. The subsequent flow of signal is the same as in the previous embodiment (shown in FIG. 15).

The operation of this embodiment will now be described. It is assumed that the laser beam emitted from laser 92 has been modulated at frequency $f_0$. This laser beam is split by half mirror 93 into transmitted and reflected laser beams. The transmitted laser beam is transmitted without change in its frequency $f_0$ through half mirror 97 to be incident on fiber 57 and be projected onto back support member 48. The reflected light beam is converted by ultrasonic shifter 95 into a modulated light beam at a frequency of $f_0+f_1$.

When the laser beam at frequency $f_0$ is projected onto back support member 48, a laser beam at a frequency of $f_0+\Delta f$, having been modulated according to the vibration of back support member 48, is reflected and led through fiber 57 to be incident on half mirror 97.

A laser beam at frequency of $f_0+f_1$ provided from ultrasonic shifter 95 (reference beam) and a laser beam at frequency of $f_0+\Delta f$ provided from fiber 57 (signal beam) are led through lens 98 onto the light incidence surface of photodiode 99, whereby they are combined for heterodyne detection. The output signal of photodiode 99 is amplified by amplifier 100 before being supplied to frequency analyzer 101. Frequency analyzer 101 calculates a frequency change $\Delta f$ produced by the vibration of back support member 48, obtains the vibration speed $V = \lambda \cdot \Delta f/2$ from $\Delta f$, and provides a DC voltage proportional to the vibration speed V. As the vibration speed V, a maximum value is used. The output of frequency analyzer 101 has the same effect as the output of rectifying/smoothing circuit 79 in the previous embodiment.

In this embodiment, it is possible to obtain accurate analysis of vibration even the reflectivity of back support member 8 or the like is changed. He-Ne laser 92 may be replaced with a semiconductor laser. The components from He-Ne laser 92 till photodiode 99 may be provided in a miniaturized form in the neighborhood of back support member 48.

Figure 23:
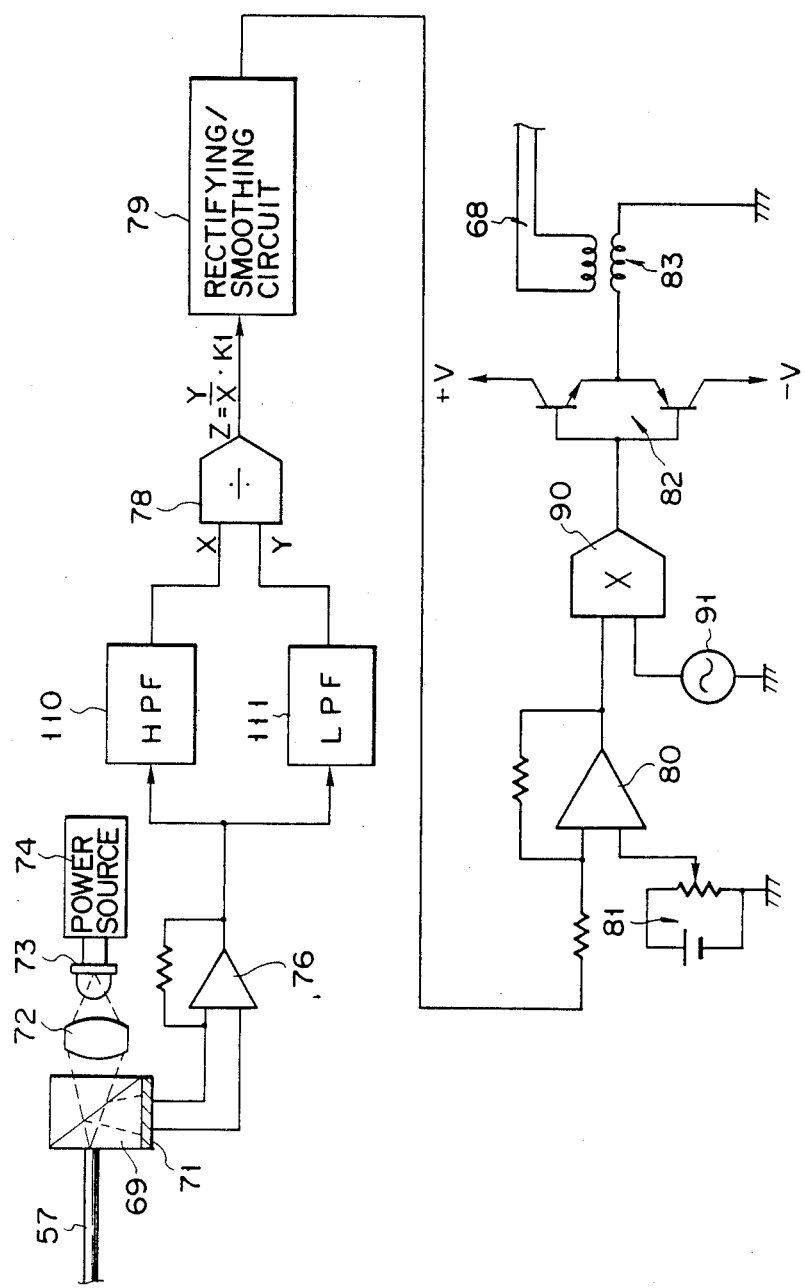
Figure 24A:
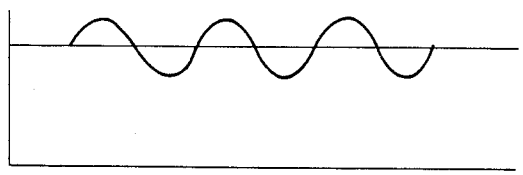
FIGS. 24(a) ~ (f) are waveform charts for explaining the operation of the ultrasonic vibration treatment apparatus of FIG. 23.
Figure 24B:
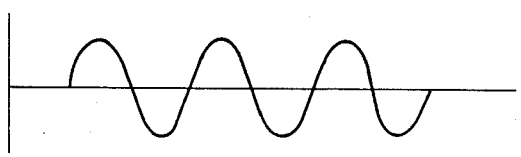
Figure 24C:
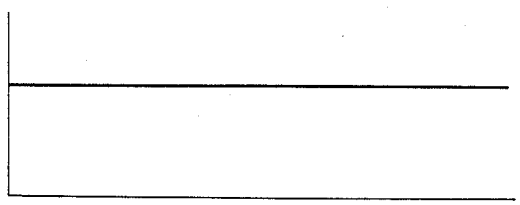
Figure 24D:
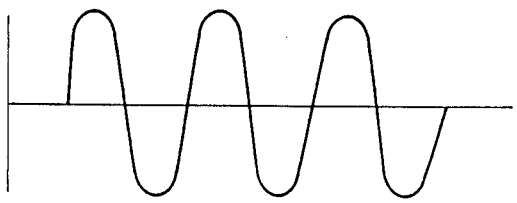
Figure 24E:
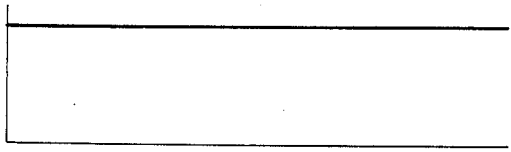
Figure 24F:
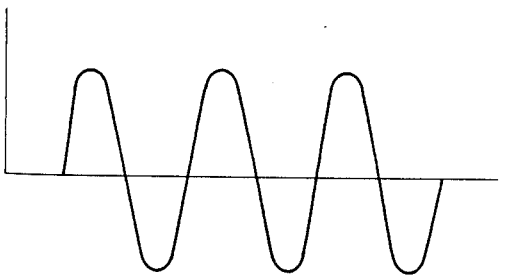

FIG. 23 shows a still further embodiment of the invention. This system is a modification of the previous embodiment of FIG. 15. In this instance, only one side of half prism 69 is provided with light-receiving element 71, and light-receiving element 70 in the previous embodiment, for receiving part of the projected beam, is absent. The output of light-receiving element 71 is supplied through amplifier 76 to HPF 110 and LPF 111. The outputs of HPF 110 and LPF 111 are coupled through divider 78 to rectifying/smoothing circuit 79. The subsequent flow of signal is the same as in the previous embodiment.

The operation of this embodiment will now be described with reference to FIG. 24. Part of the reflected light from back support member 48 is received by light-receiving element 71, the output of which is amplified by amplifier 76. The output signal of amplifier 76, as shown in (a) in FIG. 24, contains a vibration component, which is reflected when back support member 48 is vibrating, and a DC component, which is reflected when back support member 48 is not vibrating. HPF 110 removes the DC component in the output of amplifier 76 to provide a signal consisting of the sole vibration component, as shown in (b) in FIG. 24. Likewise, LPF 111 removes the vibration component in the output of amplifier 76 to provide a signal consisting of the sole DC component, as shown in (c) in FIG. 24.

The outputs of HPF 110 and LPF 111 are combined in divider 78 to obtain a signal as shown in (d) in FIG. 24. This signal is rectified and smoothed in rectifying/smoothing circuit 79 to obtain a DC signal proportional to the amplitude of vibration of back support member 48, as shown in (e) in FIG. 24. Thus, multiplier 90 produces a drive signal according to the amplitude of vibration of back support member 48 as in the previous embodiment of FIG. 15.

Figure 25A:
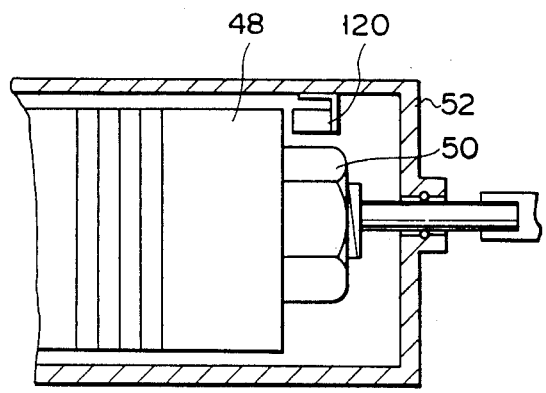
FIGS. 25(a) and 25(b) are views showing respective modifications of an optical sensor used in light projection means of the ultrasonic vibration treatment apparatus according to the invention.
Figure 25B:
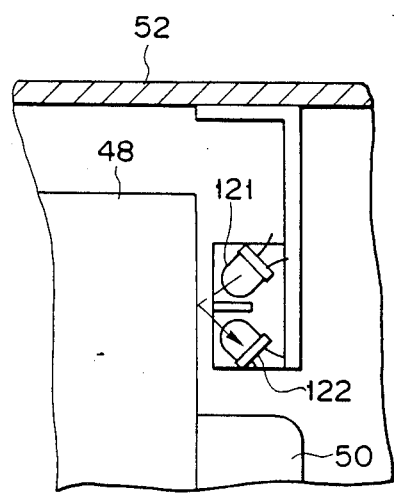

In the above description, the optical sensor for detecting the vibration is provided outside case 52. However, it is possible to mount optical sensor 120 inside case 52 in the vicinity of the rear end surface of back support member 48, as shown in FIG. 25(a). Optical sensor 120, as shown in FIG. 25(b), is a photocoupler consisting of light-emitting diode 121 and photo-transistor 122. This arrangement again permits optical contact-free measurement of the vibration of back support member 48.

As has been shown, with this embodiment of the invention, it is possible to provide a ultrasonic vibration treatment apparatus, which permits detection of the vibration of the vibrator without affecting the status of vibration through detection of the vibration of the vibrator by non-contact detection with the optical sensor, thus permitting stable control of the drive current through the vibrator.

What is claimed is:

1. An ultrasonic treatment apparatus comprising:
   a vibratory apparatus having an ultrasonic vibrator means, a housing including the ultrasonic vibrator means, and an oscillation transmitting means for transmitting the ultrasonic vibration from the ultrasonic vibrator means to an object to be treated;
   a light guide member fixed to the housing of said vibratory apparatus; and
   a control unit outside said housing of the vibratory apparatus and optically coupled to said vibratory apparatus by said light guide member, the control unit comprising:
   (a) light emitting means for generating light which is to be optically coupled for injection into one end of said light guide member;
   (b) light detecting means for detecting light optically coupled into it from said one end of the light guide member;
   (c) means for measuring the vibration of said ultrasonic vibrator means in accordance with light emitted from said light emitting means and light detected by said light detecting means; and
   (d) means for controlling the vibration of the ultrasonic vibrator means based on an output signal from said measuring means; and
   means for fixing the light guide member to the housing of said vibratory apparatus and for optically coupling said light emitting means, said light detecting means and the light guide member such that light emitted from said light emitting means is injected into said one end of the light guide member and irradiated onto said ultrasonic vibrator means through the other end of said light guide member and the light reflected from said ultrasonic vibrator means is received at the other end of said light guide member and is incident onto said light detecting means from the one end of said light guide member.

2. The apparatus according to claim 1, wherein said measuring means further includes:
   means for rectifying the output of said divider means; and
   means for calculating a difference between the output of said rectifying means and a predetermined reference value.

3. The apparatus according to claim 1, wherein said control unit includes:
   oscillating means for providing a signal at a predetermined frequency; and
   means for amplifying an output signal of said oscillating means in accordance with the output of said measuring means.

4. The apparatus according to claim 1, wherein said measuring means includes divider means for calculating a ratio between the light detected by said light detecting means and the light emitted from said light emitting means.

5. The apparatus according to claim 1, wherein said optical coupling means includes a half prism coupled between said light emitting means and the one end of said light guide member for transmitting part of the light emitted from said light emitting means to the one end of said light guide member, reflecting part of the light emitted from said light emitting means in a first direction, and reflecting in a second direction at least part of the light reflected from said ultrasonic vibrator means and exiting from the end of the light guide member after being guided through the light guide member;
   said light detecting means comprising a first light-receiving element for receiving light reflected by said half prism in said first direction and a second light-receiving element for receiving light reflected by said half prism in said second direction; and
   said measuring means includes divider means for calculating a ratio between the outputs from said first and second light-receiving elements.

6. The apparatus according to claim 5, wherein said measuring means includes:
   a low-pass filter means for extracting a DC component from the output of said first light-receiving element;
   a high-pass filter means for extracting an AC component from the output of said second light-receiving element; and
   divider means for calculating a ratio between the outputs from said low-pass filter means and said high-pass filter means.

7. The apparatus according to claim 1, wherein said fixing means includes a bushing provided on the housing and into which the light guide member penetrates, and means for sliding the bushing in the direction along which the light guide member penetrates in order to set the distance between the ultrasonic vibration means and the face of the light guide member at said other end thereof.

8. The apparatus according to claim 7, wherein said bushing is slidably engaged with a slide base which is fixed to the housing, and said sliding means comprises a pinion-rack mechanism for sliding the bushing.

* * * * *